United States Patent
Kellerman

(10) Patent No.: US 12,311,092 B2
(45) Date of Patent: *May 27, 2025

(54) VASCULAR FLOW CONTROL DEVICES AND METHODS

(71) Applicant: Avenu Medical, Inc., San Juan Capistrano, CA (US)

(72) Inventor: Brad M. Kellerman, Escondido, CA (US)

(73) Assignee: AVENU MEDICAL, INC., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/145,729

(22) Filed: Dec. 22, 2022

(65) Prior Publication Data
US 2023/0131931 A1   Apr. 27, 2023

Related U.S. Application Data

(62) Division of application No. 16/283,089, filed on Feb. 22, 2019, now Pat. No. 11,564,690.

(Continued)

(51) Int. Cl.
*A61M 1/36* (2006.01)
*A61B 17/00* (2006.01)
*A61B 17/11* (2006.01)

(52) U.S. Cl.
CPC .......... *A61M 1/3655* (2013.01); *A61B 17/11* (2013.01); *A61B 2017/00252* (2013.01); *A61B 2017/1107* (2013.01); *A61B 2017/1139* (2013.01)

(58) Field of Classification Search
CPC .......... A61B 17/11; A61B 2017/00252; A61B 2017/1107; A61M 1/3655
See application file for complete search history.

(56) References Cited

U.S. PATENT DOCUMENTS

| 5,755,779 A | 5/1998 | Horiguchi |
| 6,120,534 A | 9/2000 | Ruiz |

(Continued)

FOREIGN PATENT DOCUMENTS

WO   WO-2017011402 A1 *  1/2017  ............. A61B 17/11

OTHER PUBLICATIONS

Non-Final Office action for U.S. Appl. No. 17/027,517, filed Apr. 11, 2023, 15 pages.

(Continued)

*Primary Examiner* — Jessica Arble
*Assistant Examiner* — Hans Kaliher
(74) *Attorney, Agent, or Firm* — Stinson LLP

(57) ABSTRACT

A method of producing an arteriovenous (AV) fistula includes producing an anastomosis between a primary blood vessel (e.g., a vein) and a secondary blood vessel (e.g., an artery). A collateral (or competing) blood vessel in fluid communication with one of the primary blood vessel or the secondary blood vessel is identified. A reversible flow restrictor is then applied to the collateral blood vessel to reduce a blood flow rate through the collateral blood vessel. In some embodiments, the anastomosis can be produced percutaneously. In some embodiments, the reversible flow restriction (or a portion thereof) can be removed from the collateral blood vessel. In other embodiments, the reversible flow restriction (or a portion thereof) can be adjusted to allow increased blood flow therethrough while within the collateral blood vessel.

14 Claims, 11 Drawing Sheets

Related U.S. Application Data

(60) Provisional application No. 62/634,107, filed on Feb. 22, 2018.

(56) References Cited

U.S. PATENT DOCUMENTS

| | | | |
|---|---|---|---|
| 6,464,665 | B1 | 10/2002 | Heuser |
| 6,638,257 | B2 | 10/2003 | Amplatz |
| 8,062,321 | B2 | 11/2011 | Heuser et al. |
| 8,206,427 | B1 | 6/2012 | Ryan et al. |
| 8,888,836 | B2 | 11/2014 | Berglund |
| 9,259,340 | B2 | 2/2016 | Heuser et al. |
| 9,301,830 | B2 | 4/2016 | Heuser et al. |
| 9,439,710 | B2 | 9/2016 | Reu et al. |
| 9,452,015 | B2 | 9/2016 | Kellerman et al. |
| 9,474,562 | B2 | 10/2016 | Kellerman et al. |
| 9,486,276 | B2 | 11/2016 | Rios et al. |
| 9,522,016 | B2 | 12/2016 | Kellerman et al. |
| 10,603,040 | B1* | 3/2020 | Berman ............ A61B 18/1492 |
| 11,684,371 | B2 | 6/2023 | Allen et al. |
| 2003/0033005 | A1 | 2/2003 | Houser et al. |
| 2003/0069646 | A1 | 4/2003 | Stinson |
| 2003/0229366 | A1 | 12/2003 | Reggie et al. |
| 2004/0143315 | A1 | 7/2004 | Bruun et al. |
| 2005/0055082 | A1 | 3/2005 | Ben Muvhar et al. |
| 2007/0203515 | A1 | 8/2007 | Heuser et al. |
| 2011/0021969 | A1 | 1/2011 | Formichi |
| 2011/0257577 | A1* | 10/2011 | Lane ................. A61M 1/3653 604/6.11 |
| 2011/0264201 | A1 | 10/2011 | Yeung et al. |
| 2012/0016203 | A1 | 1/2012 | King |
| 2013/0030521 | A1 | 1/2013 | Nitzan et al. |
| 2013/0274648 | A1 | 10/2013 | Weinberger |
| 2014/0025151 | A1 | 1/2014 | Gao |
| 2014/0330367 | A1 | 11/2014 | Thapilyal |
| 2015/0134051 | A1 | 5/2015 | Donadio et al. |
| 2015/0297818 | A1 | 10/2015 | Matsubara et al. |
| 2016/0374682 | A1* | 12/2016 | Leonard ................. A61F 2/064 606/153 |
| 2017/0119464 | A1 | 5/2017 | Rios et al. |
| 2017/0202603 | A1 | 7/2017 | Cohn et al. |
| 2018/0014935 | A1 | 1/2018 | Phillips |
| 2020/0178978 | A1 | 6/2020 | Ben-Mavhar et al. |
| 2021/0177598 | A1 | 6/2021 | Matheny |
| 2022/0241565 | A1 | 8/2022 | Nae et al. |

OTHER PUBLICATIONS

Final Office action for U.S. Appl. No. 17/027,517, filed Oct. 24, 2023, 17 pages.

Non-Final Office Action for U.S. Appl. No. 17/027,517, filed Feb. 23, 2024, 16 pages.

Aal et al., Devices and Techniques for Percutaneous Creation of Dialysis Arteriovenous Fistulas, Seminars in Interventional Radiology, vol. 39, No. 1, 2022, pp. 66-74.

Final Office action for U.S. Appl. No. 17/027,517, filed Sep. 5, 2024, 16 pages.

* cited by examiner

VASCULAR FLOW CONTROL DEVICES AND METHODS

CROSS-REFERENCE TO RELATED APPLICATIONS

This application is a divisional of U.S. application Ser. No. 16/283,089 entitled "Vascular Flow Control Devices and Methods," filed Feb. 22, 2019, which claims benefit of priority to U.S. Provisional Application Ser. No. 62/634,107, entitled "Vascular Flow Control Devices and Methods," filed Feb. 22, 2018, which is expressly incorporated herein by reference in its entirety.

BACKGROUND

The embodiments described herein relate to devices and methods for controlling vascular flow. More particularly, the embodiments described herein relate to flow control devices and methods for reversibly and/or selectively controlling blood flow in collateral blood vessels associated with a fistula.

In medical practice, there is often a need to connect conduits to one another or to a replacement conduit to treat disease or dysfunction of the existing conduits. Such connections between conduits are known as an anastomosis. Some known methods for creating an anastomosis include bringing two vessels into contact with each other and joining them together with sutures or clips. Examples of anastomoses include an intestinal anastomosis, a colostomy, and an arteriovenous (AV) fistula. An AV fistula is created by connecting an artery to a vein to produce a leak-free blood flow path between the artery and vein. AV fistulas are commonly used in connection with hemodialysis and provide a connection point at which a high flow rate of blood can be withdrawn from and returned to the body. Clinical evidence has shown that an autogenous fistula provides better long-term clinical results than either a central catheter access system or a graft, so AV fistulas a desired method for vascular access.

FIG. 1 shows a schematic diagram of a known fistula 1, which includes the vein (also referred to as a primary vessel PV) coupled to the artery (also referred to as a secondary vessel SV). The fistula 1 includes an aperture 3 that allows blood to bypass from the secondary vessel SV to the primary vessel PV, as shown by the arrows in FIG. 1. The blood is withdrawn through a large access needle near the secondary vessel SV and is transported via a withdraw line 171 to a dialysis machine. The blood is processed by the dialysis machine to remove waste products and is returned to the primary vessel PV via a return line 172 and a second large return needle. The primary vessel PV forms an outlet flow path $FP_{out}$ through which the returned blood flows back towards the patient's heart. Although the fistula 1 is shown in FIG. 1 as being in a forearm, known methods also include establishing a fistula in the upper arm, near the wrist, in the thigh, and in rare cases, elsewhere in the body. Moreover, there are different methods for joining the adjacent vessels to produce a fistula. For example, the fistula can be an end-to-side fistula (see FIG. 2A), an end-to-end fistula (see FIG. 2B), or a side-to-side fistula (see FIG. 2C).

Because known dialysis machines and methods operate with high blood flow rates to accommodate shorter, high-efficiency sessions, known fistulas are targeted to achieve a flow rate of 500 ml per minute or greater during the entire dialysis procedure (often between 3 and 5 hours). Additionally, the segment of the primary vessel PV (e.g., the vein) in which the fistula is created generally needs to be long enough to allow adequate separation of the access needle and the return needle to prevent recirculation of dialyzed and non-dialyzed blood between the two needles. Such lengths should be about 6 cm or greater. To achieve these desired flow performance characteristics, known procedures for creating an AV fistula include allowing the newly created fistula to mature prior to being used for dialysis. Fistula maturation involves remodeling of the blood vessels (both the artery and the vein), which is triggered by the increased blood flow and accompanying change in hemodynamic forces. During the maturation process, which can take 3-4 months, the blood flow will increase to suitable levels, the diameter of the primary vessel will increase to a suitable size (e.g., at least about 4 mm), and the wall thickness of the primary vessel will increase to allow repeated cannulation. The maturation process is shown schematically in FIGS. 3A-3C, which show the primary vessel PV (e.g., the vein) and the secondary vessel SV (e.g., the artery) prior to being joined (FIG. 3A), the primary vessel PV and the secondary vessel SV as initially joined to create the fistula 1 (FIG. 3B), and the subsequent increase in the diameter of the primary vessel SV as a result of fistula maturation (FIG. 3C).

Known methods for surgically creating a fistula include first identifying the target vein and artery. The selected vein is then dissected and joined to the selected artery via sutures to create the fistula. Known surgical methods typically include ligation of any competing (also referred to as collateral) outflow veins that may direct flow away from the desired vein (i.e., the primary vessel) that is intended for dialysis. If the blood flow is split between too many vessels, a single outflow vein may not have sufficient flow to fully mature and/or support dialysis. Although such procedures may increase the likelihood that the selected vein will successfully mature, they also render the ligated veins permanently unusable. Accordingly, if the selected vein fails to mature, a new fistula must be created with entirely different vessels. For example, it is not uncommon for fistulas created via known surgical techniques to fail to mature due to stenosis associated with dissection and suturing.

Recently, new methods have been developed to create an autogenous fistula percutaneously. Percutaneous methods are disclosed, for example, in U.S. Pat. No. 9,439,710 entitled "Intravascular Arterial to Venous Anastomosis and Tissue Welding Catheter," which is expressly incorporated by reference in its entirety. Such percutaneous methods eliminate the need to surgically dissect the vein, suture it to the artery, and permanently ligate the competing veins. Since no veins are ligated during such percutaneous procedures, the resulting fistula can include multiple outflow veins. This is shown schematically in FIG. 4, which shows the inlet flow path $FP_{in}$ within the secondary vessel SV, the fistula 1, and the outlet flow path $FP_{out}$ in the primary vessel PV. FIG. 4 also shows three competing (or collateral) outlet vessels, $CV_1$, $CV_2$, and $CV_3$. As a result of competing vessels, some percutaneously created fistulas can require additional time to mature for dialysis access.

Thus, a need exists for improved methods and devices for promoting the maturation of a fistula having multiple outflow vessels while still preserving the patency of the outflow vessels for potential future use.

SUMMARY

The embodiments described herein address the foregoing problem by providing a reversible restriction to reduce the flow in competing outflow veins, thereby directing flow into the intended vein for dialysis. As a result, the embodiments described herein can reduce the amount of time it takes for the vessel to mature, while also preserving surrounding vasculature for possible later use.

In some embodiments, a vascular flow control system includes a reversible flow restrictor comprising an expandable structure or basket having at least one tissue contacting surface thereon. The flow restrictor is adapted to be disposed in a blood vessel. The tissue contacting surface may comprise an anchoring member. The flow restrictor further comprises a first orifice on an upstream end of the flow restrictor and a second orifice on a downstream end of the flow restrictor. Advantageously, the reversible flow restrictor is manipulable after being fixedly disposed in a blood vessel to increase fluid flow capacity through the blood vessel. In certain embodiments, the reversible flow restrictor is manipulable by adjusting the size of one or both of the first and second orifices. To increase the flow rate capacity, adjusting the size of one or both of the first and second orifices means increasing the size of one or both of the first and second orifices. Alternatively, the reversible flow restrictor is manipulable by reducing a size, such as a diameter, of the expandable structure, which increases fluid flow capacity through the blood vessel, and may permit withdrawal of the reversible flow restrictor from its site in the vessel. The at least one anchoring member may comprise tines formed into the outside of the expandable structure, the tines being configured to pierce an internal wall of the blood vessel to prevent movement of the flow restrictor within the blood vessel. In some embodiments, the second orifice is narrower than the first orifice when the expandable structure or basket is in an expanded configuration. A membrane covers at least a portion of the expandable structure or basket of the flow restrictor. The expandable structure or basket may be made from a shape memory material such as Nitinol®, or may be constructed from a single piece of tubing and heat set into a desired shape.

In some embodiments, the membrane can be a thin, polymeric membrane, which is perforated, or configured to promote tearing or deformation to expand its diameter. In some embodiments, the membrane may be made up of a dip-coated polymer, such as latex. It may be coated with an immunosuppressive or antineoplastic agent such as sirolimus or paclitaxel, respectively, to prevent stenosis, or heparin to prevent thrombus formation. The membrane may alternatively be comprised of a braided shape memory allow structure.

In some embodiments, the vascular flow control system is a part of a kit that includes a plurality of reversible flow restrictors and a delivery system for delivering the flow restrictors to a desired site in a blood vessel. Each reversible flow restrictor from the plurality of reversible flow restrictors includes an anchor portion and a valve portion, the anchor portion being configured to be secured within a collateral blood vessel in fluid communication with one of the primary blood vessel or the secondary blood vessel, the valve portion defining at least one flow orifice. The valve portion is configured such that a flow rate through the valve portion can be changed after the reversible flow restrictor is secured within the collateral blood vessel. The delivery system includes a delivery catheter having a distal tip having a center lumen with a tapered dilator. The delivery catheter can include a moveable outer sheath that constrains the expandable structure or basket of the flow restrictor in a collapsed configuration during delivery, and that releases the expandable structure or basket when the flow restrictor is at the desired site.

In some embodiments, a method for creating an arteriovenous (AV) fistula includes selecting an appropriate procedural site having each of a primary blood vessel and a secondary vessel in close proximity to one another. The method includes creating an arteriovenous fistula between the primary vessel and the secondary vessel. An outflow vessel that is not to be immediately used as a dialysis access is then selected and a flow restrictor is inserted into the selected outflow vessel for reducing blood flow therethrough. The flow restrictor can be inserted using a delivery system, such as a delivery catheter having a distal tip with a center lumen. The distal tip includes a tapered dilator, and the delivery catheter can be moved to the selected outflow vessel and then to a desired location within the selected outflow vessel.

In some embodiments, the method may further comprise expanding the flow restrictor within the selected outflow vessel at the desired location. Another optional step involves fixing the flow restrictor in place at the desired location by securing anchoring members, such as tines, to an inner wall of the selected outflow vessel. The delivery catheter is then withdrawn from the selected outflow vessel, leaving the flow restrictor in place.

In some embodiments, the method can further include collapsing the flow restrictor and removing the flow restrictor from the selected outflow vessel. In other embodiments, the flow restrictor can be maintained within the selected outflow vessel, but can be expanded to allow an increased flow therethrough. In this manner, the flow restrictor is reversible, and patency of the selected outflow vessel is preserved for its later use as a primary dialysis access site.

DETAILED DESCRIPTION

Figure 1:
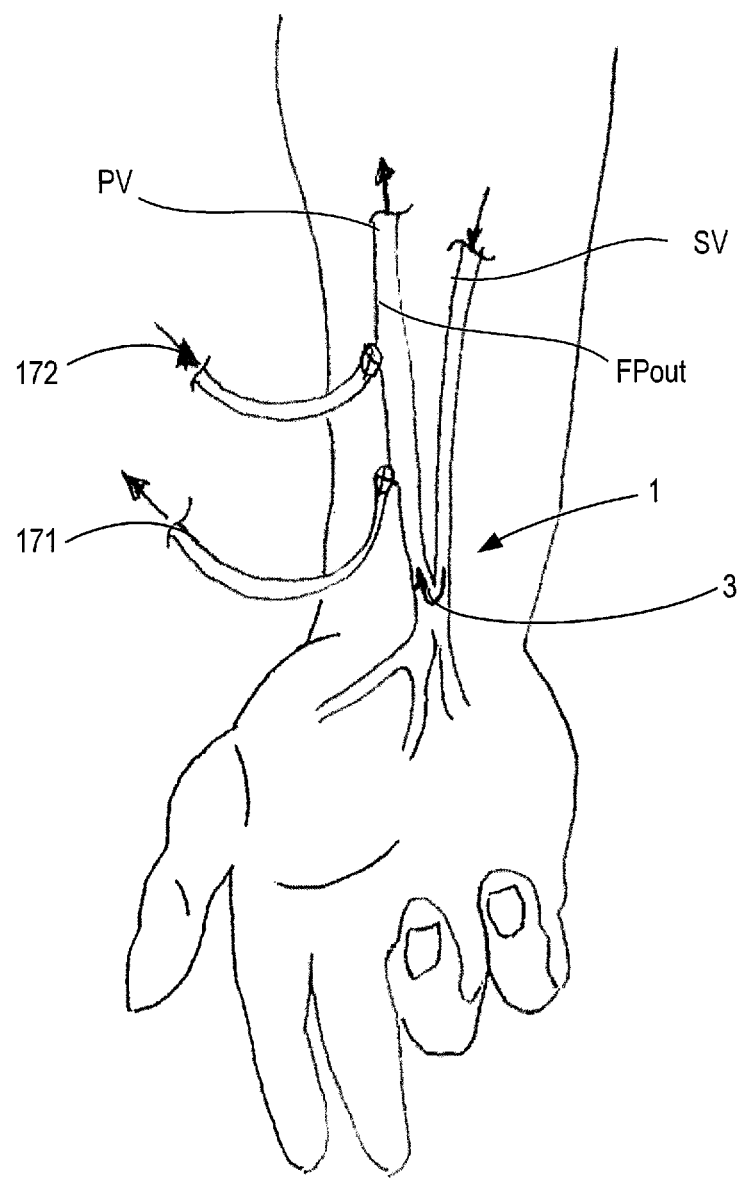
FIG. 1 shows a schematic illustration of a known arteriovenous (AV) fistula.
Figure 2A:
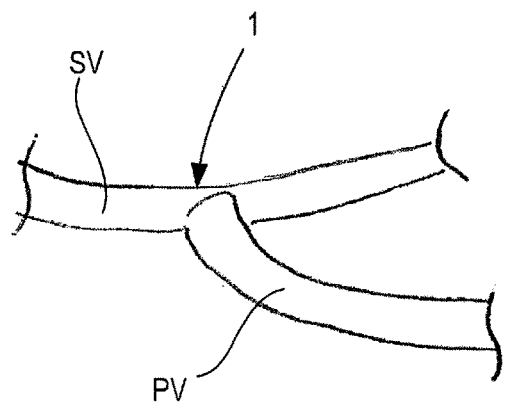
FIGS. 2A-2C are schematic illustrations of various fistula types, including an end-to-side fistula (FIG. 2A), an end-to-end fistula (FIG. 2B), or a side-to-side fistula (FIG. 2C).
Figure 2B:
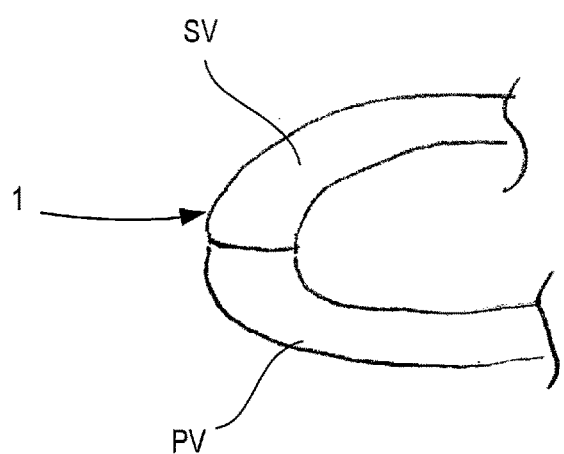
Figure 2C:
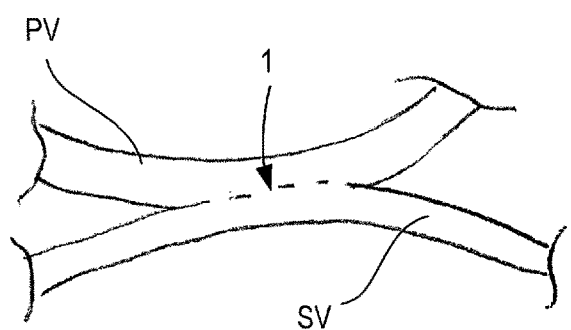
Figure 3A:
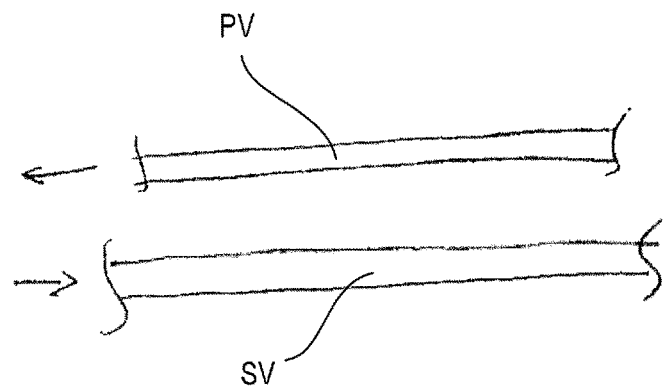
FIGS. 3A-3C are schematic illustrations of the fistula maturation process, including showing a primary vessel and a secondary vessel SV prior to being joined (FIG. 3A), the primary vessel and the secondary vessel as initially joined (FIG. 3B), and the subsequent increase in the diameter of the primary vessel as a result of fistula maturation (FIG. 3C).
Figure 3B:
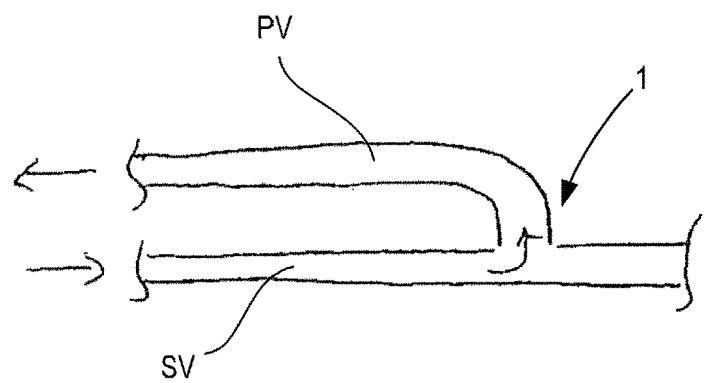
Figure 3C:
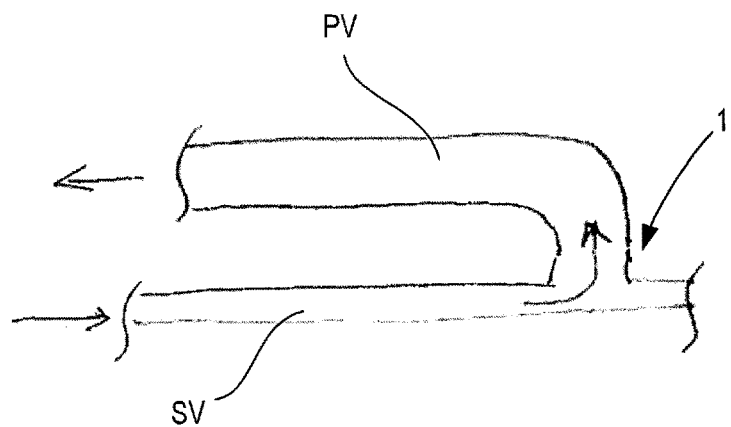
Figure 4:
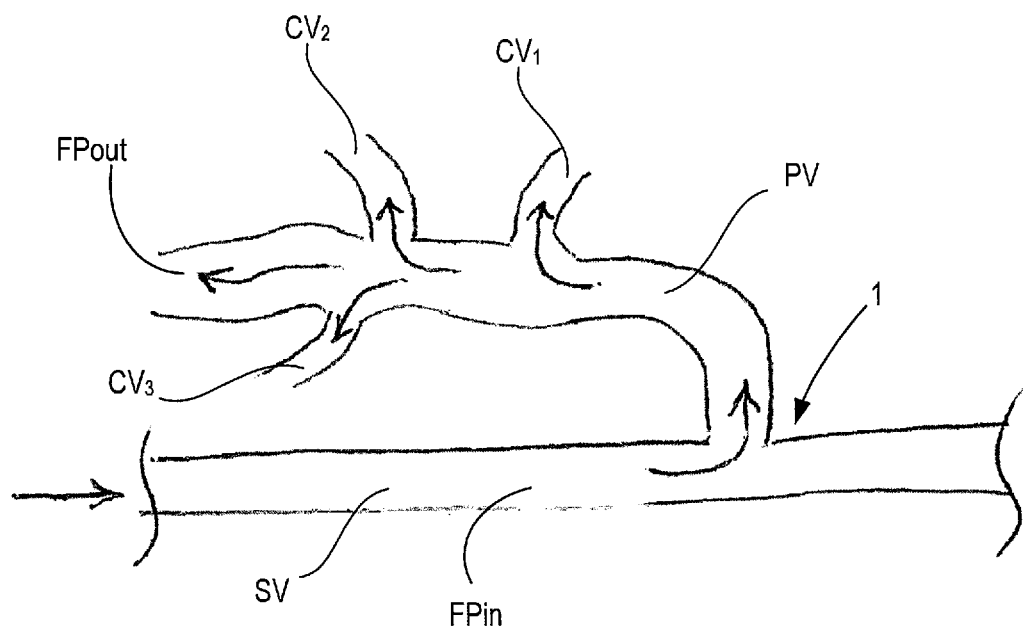
FIG. 4 is a schematic illustration of a fistula having multiple competing (or collateral) outlet vessels.

Reversible flow restrictors and methods for enhancing and/or modifying an AV fistula are described herein. Specifically, the devices, methods, and kits described herein facilitate placing a reversible restriction in the vasculature to reduce the flow in competing outflow veins. In this manner, a greater amount of the flow through the fistula is directed into the intended vein for dialysis. As a result, the embodiments described herein can reduce the amount of time it takes for the vessel to mature, while also preserving vasculature for possible later use.

In some embodiments, a method of producing an arteriovenous (AV) fistula includes producing an anastomosis between a primary blood vessel (e.g., a vein) and a secondary blood vessel (e.g., an artery). A collateral (or competing) blood vessel in fluid communication with one of the primary blood vessel or the secondary blood vessel is identified. A reversible flow restrictor is then applied to the collateral blood vessel to reduce a blood flow rate through the collateral blood vessel. In some embodiments, the anastomosis can be produced percutaneously. In some embodiments, the reversible flow restriction (or a portion thereof) can be removed from the collateral blood vessel. In other embodiments, the reversible flow restriction (or a portion thereof) can be adjusted to allow increased blood flow therethrough while remaining within the collateral blood vessel.

Any of the devices, kits, or methods described herein can be used to enhance or improve the performance of an existing AV fistula. For example, in some embodiments, a method of enhancing an existing arteriovenous (AV) fistula includes assessing a flow performance of a primary outflow path defined within a primary vein of the existing AV fistula. A collateral vein in fluid communication with the primary vein is then identified. The method further includes manipulating, in response to the assessment, a reversible flow restrictor within one of the collateral vein or the primary vein to change a blood flow rate within the primary outflow path. In some embodiments, the manipulation can include inserting the reversible flow restrictor into the collateral vein or the primary vein. In other embodiments, the manipulation can include changing a flow restriction of the reversible flow restrictor that was previously placed in the collateral vein or the primary vein.

In some embodiments, a kit for creating and/or enhancing an AV fistula includes a set of reversible flow restrictors and a delivery catheter. Each of the reversible flow restrictors includes an anchor portion and a valve portion. The anchor portion is configured to be secured within a collateral (also referred to as competing) blood vessel in fluid communication with one of a primary blood vessel (e.g., a vein) or a secondary blood vessel (e.g., an artery) of the AV fistula. The valve portion defines at least one flow orifice and is configured such that a flow rate through the valve portion can be changed after the reversible flow restrictor is secured within the collateral (or competing) blood vessel. The delivery catheter is configured to percutaneously deliver one of the reversible flow restrictors from the set of flow restrictors to the collateral blood vessel. In some embodiments, the kit can include multiple different sets of reversible flow restrictors, each having a different size and/or nominal flow rate. In this manner, the kit provides different options for the practitioner that can be used for a given anatomical situation or desired performance.

The term "about" when used in connection with a referenced numeric indication means the referenced numeric indication plus or minus up to 10 percent of that referenced numeric indication. For example, "about 100" means from 90 to 110.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls or structural components. Such a set of walls or structural components can include, for example, multiple portions that are either continuous or discontinuous from each other. A set of walls or structural components can also be fabricated from multiple items that are produced separately and are later joined together (e.g., via a weld, an adhesive, or any suitable method).

As used herein, the terms "competing vessel" and "collateral vessel" are used interchangeably to refer to any vessel within the body that is not the primary vessel or the secondary vessel. Accordingly, in the context of an AV fistula, the primary vessel can be vein and the secondary vessel can be an artery. A competing vessel or collateral vessel are any other vessels (veins or arteries) that are not the primary or secondary vessels. Competing or collateral vessels can include, for example, side-branch vessels (e.g., a vessel that branches from either the primary vessel or the secondary vessel), an accessory vessel (e.g., an accessory vein), or any other adjacent vessel that is or can be in fluid communication with either the primary vessel or the secondary vessel.

Figure 6A:
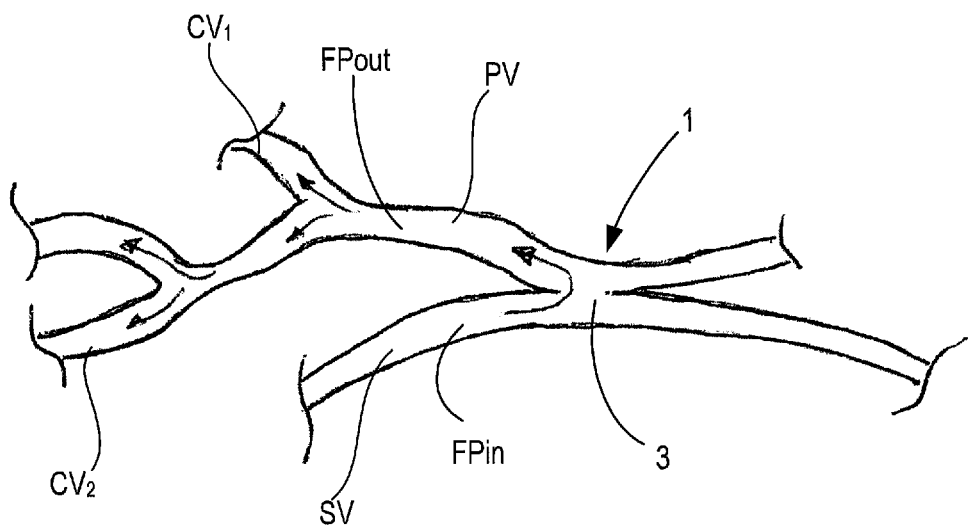
FIGS. 6A-6C are schematic illustrations of a vascular system including an AV fistula within a reversible flow restrictor according to an exemplary embodiment.
Figure 5:
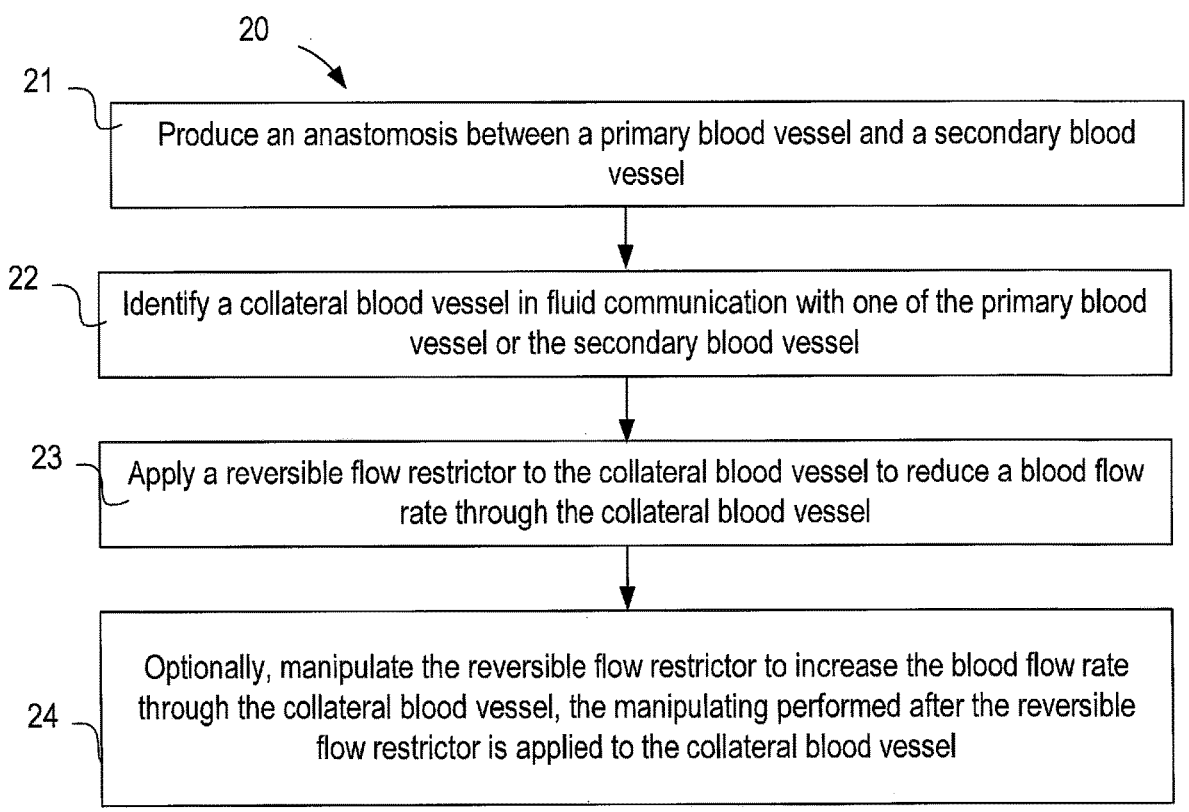
FIG. 5 is a flow chart illustrating a method of a creating an AV fistula according to an exemplary embodiment.
Figure 6B:
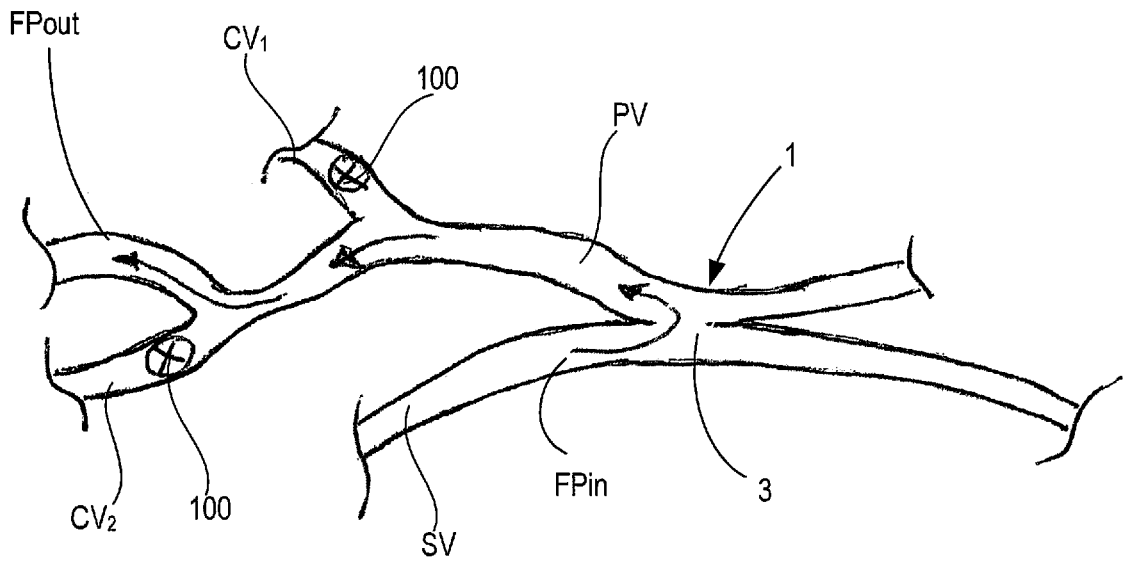
Figure 6C:
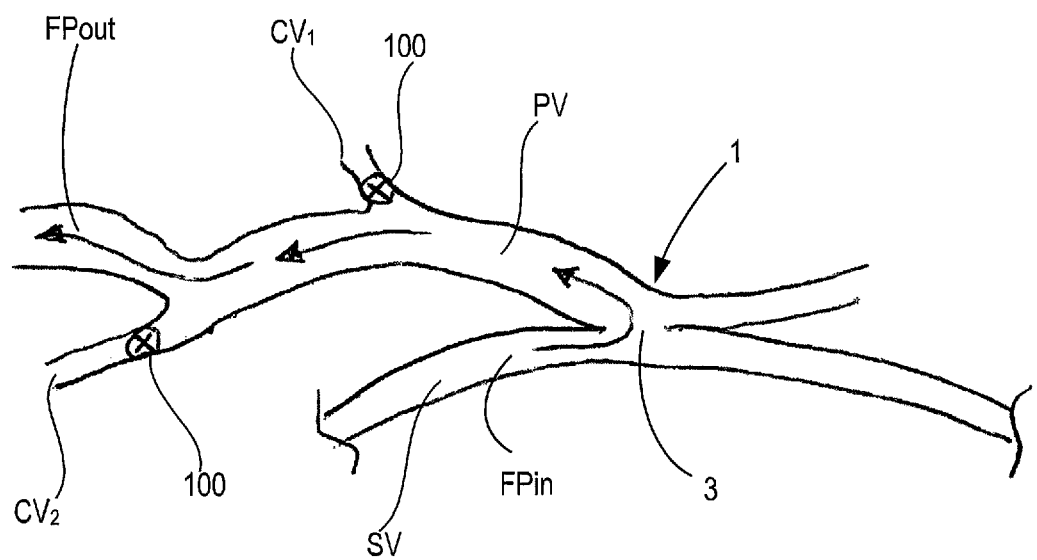

FIG. 5 is a flow chart of a method 20 of creating an arteriovenous (AV) fistula according to an exemplary embodiment. FIGS. 6A-6C are schematic illustrations of the vasculature illustrating various operations of the method 20, or other methods described here. In the following description, reference to method steps is made to FIG. 5, and reference to structural items (e.g., a primary vessel PV) refers that which is shown in FIGS. 6A-6C. The method 20 is not limited to the specific arrangement shown in FIGS. 6A-6C, but can be used to create a variety of different AV fistulas. For example, although FIGS. 6A-6C show a side-to-side fistula 1, in other embodiments, the method 20 can be used to create any other suitable fistula (e.g., end-to-end or end-to-side).

The method 20 includes producing an anastomosis between a primary vessel PV and a secondary vessel SV, at 21. As shown in FIGS. 6A-6C, this results in an inlet flow path $FP_{in}$, a flow path (or communicating aperture 3) between the primary vessel PV and the secondary vessel SV, and a primary outlet flow path $FP_{out}$. In some embodiments, the anastomosis is produced non-surgically. Similarly stated, in some embodiments, the anastomosis is produced via a minimally-invasive procedure (i.e., a procedure that does not require producing a skin incision, other than an opening required for placement of a vascular access device). Said another way, in some embodiments, the anastomosis is produced percutaneously. Such minimally-invasive methods can be any of the methods shown and described in U.S. Pat. No. 9,439,710 entitled Intravascular Arterial to Venous Anastomosis and Tissue Welding Catheter (the '710 patent) and/or U.S. patent application Ser. No. 16/219,759 and entitled Systems and Methods for Percutaneous Access, Formation, and Maintenance of Arteriovenous Fistulas (the '759 application) each of which is expressly incorporated by reference in its entirety.

For example, in some embodiments, the anastomosis can be produced using a catheter assembly of the types shown and described in the '710 patent or the '759 application. In such embodiments, the anastomosis is produced by positioning a distal end of a catheter assembly to engage an inner surface of a side wall of the primary vessel PV. The primary vessel PV is then moved into engagement with the secondary vessel SV. A piercing member is then extended from the distal end of the catheter assembly, through the side wall of the primary vessel PV and the side wall of the secondary vessel SV to produce the communicating aperture 3 between the primary vessel PV and the secondary vessel SV. In some embodiments, the fistula can be a side-to-side fistula.

Referring to FIG. 5, a collateral vessel in fluid communication with one of the primary vessel PV or the secondary vessel SV is identified, at 22. As shown in FIGS. 6A-6C, when the fistula 1 is created, one or more collateral vessels can remain intact and in fluid communication with the primary vessel PV or the secondary vessel SV. Although only two collateral vessels (identified as the first collateral vessel $CV_1$ and the second collateral vessel $CV_2$) are shown in FIGS. 6A-6C, in other embodiments, there can be any number of collateral vessels. Moreover, although the first collateral vessel $CV_1$ and the second collateral vessel $CV_2$ are shown as being in fluid communication with the primary vessel PV, in other embodiments a collateral vessel can be in fluid communication with the secondary vessel SV.

As shown by the arrows in FIG. 6A, the first collateral vessel $CV_1$ and the second collateral vessel $CV_2$ each compete with the desired primary outlet flow path $FP_{out}$ for the blood flowing through the fistula. As such, in certain instances, the lower blood flow through the primary outlet flow path $FP_{out}$ can delay or inhibit maturation of the primary vessel. To increase the likelihood that the fistula will properly mature, the method 20 also includes applying a reversible flow restrictor 100 to the collateral vessel to reduce (or stop) a blood flow rate through the collateral vessel, at 23. In some embodiments, a reversible flow restrictor 100 can be applied to any number of collateral vessels. For example, referring to FIG. 6B, in some embodiments, the method includes applying a reversible flow restrictor 100 two collateral vessels (specifically, the first collateral vessel $CV_1$ and the second collateral vessel $CV_2$).

By applying the reversible flow restrictor 100, the blood flow within the collateral (or competing) vessel can be reduced (or temporarily stopped) in a manner than can later be reversed. In this manner, the flow can be enhanced or regulated within the primary outlet flow path $FP_{out}$ without permanently ligating the collateral vessels. Similarly stated, this method can reduce the flow through competing vessels to ensure that the flow through the primary outlet flow path $FP_{out}$ is above a desired level, while still maintaining the patency of the collateral vessels for possible later use. Such later use may be desired, for example, if all or portions of the initially-selected primary outlet flow path $FP_{out}$ fail to mature. In such instances, as described herein, it may be beneficial to reverse the flow restriction in one of the collateral vessels to establish an alternative primary outlet flow path $FP_{out}$. The current method accommodates this flexibility by maintaining the collateral vessels intact.

The reversible flow restrictor 100 can be any suitable flow restrictor as shown or described herein, and can be applied to the collateral vessel in any suitable manner as described herein. For example, in some embodiments, the reversible flow restrictor can be applied by inserting the reversible flow restrictor (or a portion thereof) into the selected collateral vessel. For example, in some embodiments, the reversible flow restrictor 100 can be advanced into the collateral blood vessel using a delivery catheter (see, e.g., the delivery catheter 250 shown in FIG. 12). The delivery catheter can be manipulated to expand an anchor (or securing) portion of the reversible flow restrictor 100 to secure the restrictor at a target location within the collateral vessel. The catheter can then be withdrawn, leaving the reversible flow restrictor 100 in the desired position.

The reversible flow restrictor 100 can be applied to the collateral vessel at any suitable time. For example, in some embodiments, the flow restrictors 100 can be placed substantially contemporaneous with the creation of the AV fistula. For example, when the AV fistula is created the practitioner can select a desired (or preferred) primary outlet flow path $FP_{out}$ within the primary vessel, based on any suitable evaluation technics (ultrasound, venography, analyzing a fistulagram, or the like). The practitioner can then, along with creating the AV fistula, apply one or more reversible flow restrictors to those collateral vessels identified as potentially inhibiting the maturation of the primary outlet flow path $FP_{out}$. In other embodiments, however, the reversible flow restrictors 100 can be placed after (or in a different procedure than) the creation of the AV fistula. For example, in some embodiments, the AV fistula can be created, and the practitioner can refrain from selecting a desired (or preferred) primary outlet flow path $FP_{out}$ within the primary vessel at that time. The practitioner can then evaluate the newly created fistula after an initial time period (e.g., at least 1 week, at least about 2 weeks, at least about 3 weeks, at least bout 4 weeks, and any range therebetween) and then select the desired primary outlet flow path $FP_{out}$. The practitioner can then, at that time, apply one or more reversible flow restrictors to those collateral vessels identified as potentially inhibiting the maturation of the primary outlet flow path $FP_{out}$. In some embodiments, the method 20 can optionally include manipulating, at a later (or second) time after the initial placement (or the first time), the reversible flow restrictor to increase the blood flow rate through the collateral vessel, at 24. Similarly stated, in some embodiments, the method 20 can include reversing the effects of the reversible flow restrictor applied to the collateral vessel.

Figure 7:
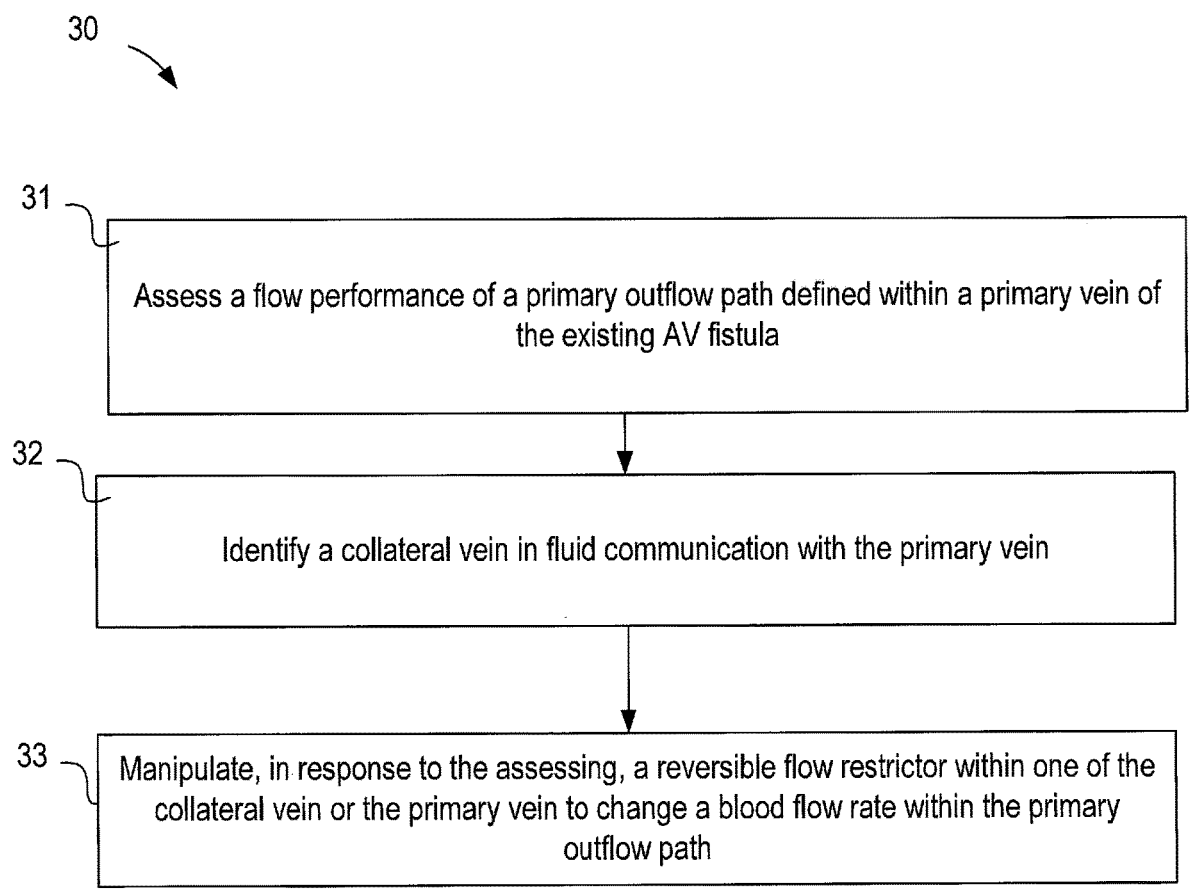
FIG. 7 is a flow chart illustrating a method of modifying a flow path of an AV fistula according to an exemplary embodiment.

In some embodiments, a method need not include creating an AV fistula, but rather can include assessing, enhancing and/or repairing an existing AV fistula. For example, FIG. 7 is a flow chart of a method 30 of enhancing performance of an arteriovenous (AV) fistula according an embodiment. The method 30 can be performed with a variety of different AV fistulas (side-to-side, end-to-end or end-to-side). The method 20 includes assessing a flow performance of a primary outflow path defined within a primary vein of the existing AV fistula, at 31. The assessing can include characterizing a maturity of the existing AV fistula by evaluating any suitable data or information. For example, in some embodiments, the assessing can include determining a size of the primary vein, determining the blood flow rate within the primary outflow path, or characterizing a magnitude of a thrill produced by the existing AV fistula. Moreover, the assessing can be performed within any suitable time period after the creation of the AV fistula. For example, in some embodiments, the assessing can be performed within about 1 week after the creation of the AV fistula. In other embodiments, the assessing can be performed within about 2 weeks, within about 3 weeks, or within about 4 weeks after the creation of the AV fistula. The assessing can be based on any suitable evaluation techniques (ultrasound, venography, analyzing a fistulagram, or the like).

The method 30 further includes identifying a collateral vein in fluid communication with the primary vein, at 32. The collateral vein can be, for example, similar to the collateral vessels shown in FIGS. 6A-6C, and can be receiving blood flow from (or competing with) the primary outflow path. In response to the assessing, a reversible flow restrictor within one of the collateral vein or the primary vein is manipulated to change a blood flow rate within the primary outflow path, at 33. For example, in some embodiments, the reversible flow restrictor can be manipulated when the existing AV fistula has not properly matured or is otherwise not performing in a suitable manner. Similarly stated, in some embodiments, the reversible flow restrictor can be manipulated when the existing AV fistula is characterized, based on the assessment, as being below a target maturity level. For example, in some embodiments, the reversible flow restrictor can be manipulated when the diameter of the primary vein is not within a desired size range (e.g., at least 4 mm; at least 6 mm). In other embodiments, the reversible flow restrictor can be manipulated when the blood flow within the primary outflow path is less than about 400 ml per minute; 500 ml per minute, or 600 ml per minute. In yet other embodiments, the reversible flow restrictor can be manipulated when assessment reveals stenosis of the primary vein.

The reversible flow restrictor can be any suitable flow restrictor as shown or described herein, and can be manipulated to change the blood flow therethrough in any suitable manner as described herein. For example, in some embodiments, the reversible flow restrictor can be removed from the vessel to obviate any flow restriction produced by the flow restrictor. Because, in some instances, an anchoring portion of the flow restrictor may be subject to tissue ingrowth at the vessel walls, and therefore may not be easily removable, in other embodiments, the reversible flow restrictor can be manipulated within the vessel to increase (or further decrease) the flow therethrough.

For example, in some embodiments, the step of manipulating the reversible flow restrictor includes increasing a size of a flow orifice to change the blood flow rate within the primary outflow path. For example, in some embodiments, a reversible flow restrictor within a collateral vessel can be manipulated to reduce the flow in the initially-selected primary outflow path to create an alternative (or new) primary outflow path. This can be desired, for example, if the initially-selected primary outflow path is damaged or is not functioning properly. In other embodiments, a reversible flow restrictor within the primary vein can be manipulated to further increase the flow in the initially-selected primary outflow path.

The flow orifice of the reversible flow restrictor can be increased by any suitable mechanism. For example, in some embodiments, the size can be increased by advancing an expandable catheter assembly to the reversible flow restrictor and expanding a portion of the catheter assembly within the orifice to deform the orifice. In some embodiments, the reversible flow restrictor can include a valve portion that includes an expandable structure that defines the flow orifice and a membrane about the expandable structure. The expandable structure can be constructed from a shape memory alloy (such as Nitinol®) and can be maintained in a low-flow (or collapsed) configuration by the membrane (see e.g., the flow restrictor 300 described below). Thus, when the membrane is deformed or removed, the expandable structure can revert to its high-flow (or expanded) configuration. Accordingly, in some embodiments, the manipulating includes deforming the membrane. In some embodiments, the reversible flow restrictor can include a valve portion that includes a structure that defines set of orifices and a membrane about the structure that obstructs a portion of the flow orifices (see, e.g., the flow restrictor 400). In in some embodiments, the manipulating includes deforming the membrane to expose the portion of the flow orifices to increase the overall flow.

FIGS. 8-11 show a reversible flow restrictor 200 according to an embodiment that can be used in connection with any of the methods or included within any of the kits described herein. The flow restrictor 200 includes an anchor portion 210 and a valve portion 230. The anchor portion 210 includes an expandable structure 211 (also referred to a basket). In some embodiments, the expandable structure 211 can extend throughout the entire flow restrictor 200 (i.e., and be included within the valve portion 230), whereas in other embodiments, the expandable structure 211 is limited solely to the anchor portion 210. The anchor portion 210 includes a set of tines 213 or anchors that can be coupled to the inside of the vessel wall to limit movement. In some embodiments, the tines 213 can engage or dig into the vessel wall. In other embodiments, the anchor portion 210 can use other mechanism for securing the flow restrictor 200 within the vessel. The anchor portion 210 is at one end of the restrictor 200 and defines an inlet flow orifice 212.

The valve portion 230 can include an underlying structure 231 that defines an outlet flow orifice 232. The structure 231 can be monolithically constructed with (or be an extension of) the expandable structure 211. In other embodiments, however, the valve structure 231 can be a separately-constructed structure. In some embodiments, the expandable structure 211 (or any of the expandable structures described herein or the valve structure 231 (or any of the valve structures described herein) can be constructed from a shape memory alloy (or super elastic alloy), such as Nitinol®.

The valve portion 230 also includes a membrane 233 that is disposed about the valve portion. In this manner, the blood flow is directed from the inlet opening 212 through the outlet flow orifice 232 without bypassing through the side lattice openings or other openings of the structure 231. In some embodiments, the membrane 233 (or any of the membranes herein) can be constructed from a dip coated polymer, such as latex or similar material. However other materials such as PTFE can be used. In order to prevent thrombus from forming on the downstream side of the restriction, in some embodiments, small holes can be cut in the membrane to allow a small amount of flow through. In another embodiment, an agent such as paclitaxel, sirolimus, or heparin may be applied to the polymer to prevent stenosis and thrombus formation. The membrane may also comprise a braided Nitinol structure.

Figure 8:
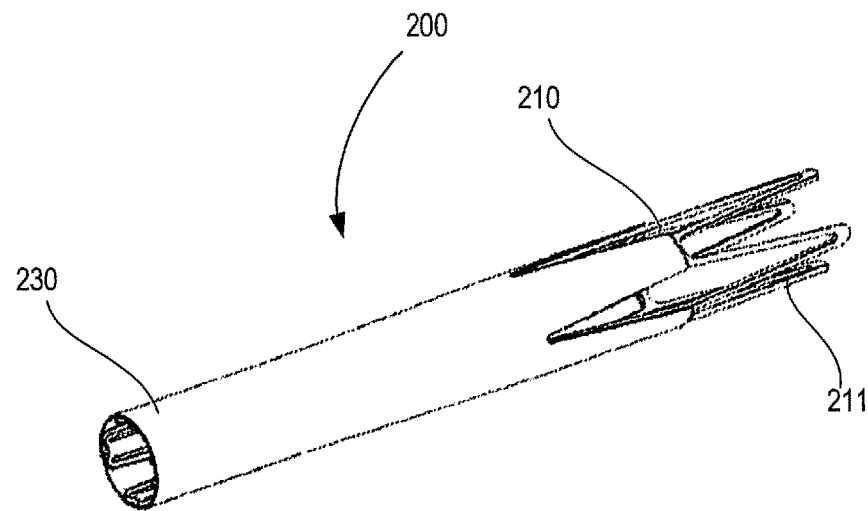
FIGS. 8 and 9 are perspective views of a reversible flow restrictor according to an embodiment in a collapsed configuration (FIG. 8) and an expanded configuration (FIG. 9).
Figure 9:
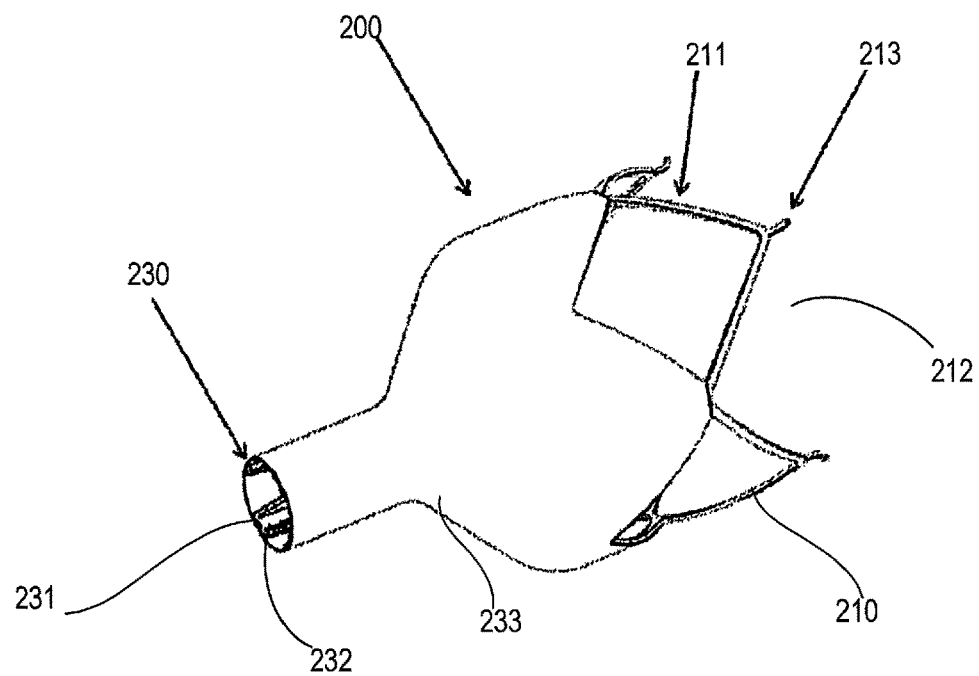
Figure 10:
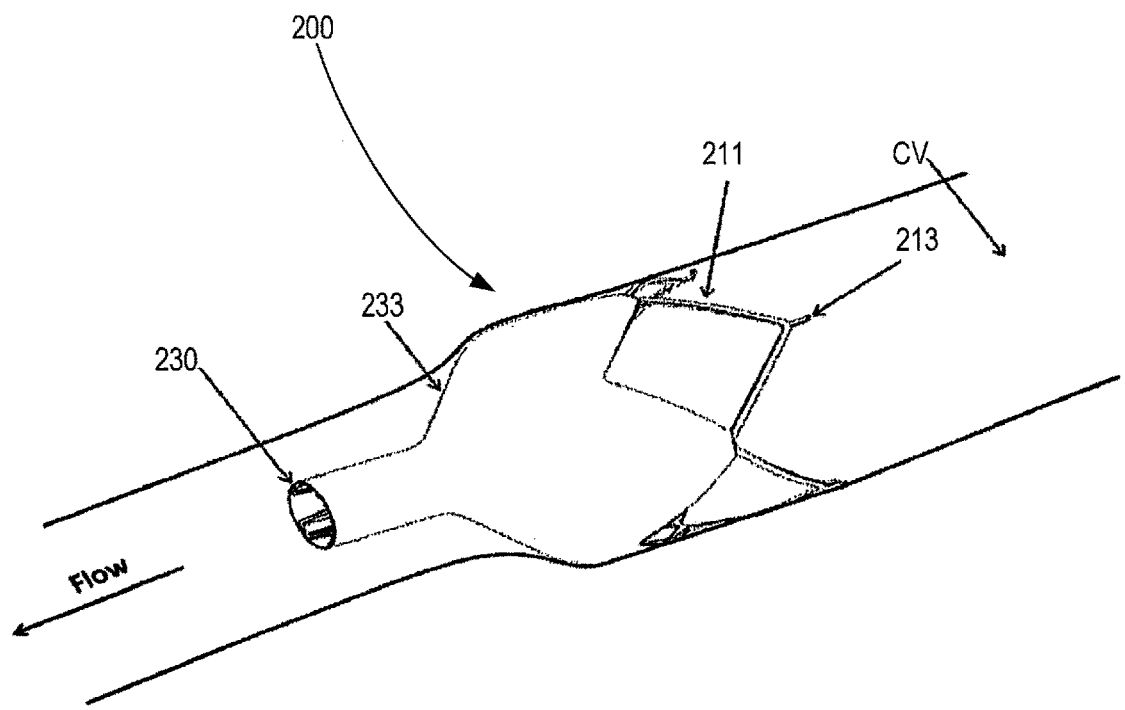
FIG. 10 is a perspective view of the reversible flow restrictor shown in FIGS. 8 and 9 deployed in a vessel in a first restriction configuration.

In use the flow restrictor 200 can be inserted into a vessel, such as a collateral vessel CV, in accordance with any of the methods described herein. Referring to FIG. 8, the flow restrictor 200 can be inserted while in a collapsed configuration. For example, in some embodiments, the flow restrictor 200 can be inserted using the catheter assembly 250 shown and described herein. Referring to FIG. 10, the flow restrictor 200 can be anchored at the desired position in the collateral vessel CV by expanding the anchor portion 210 and allowing the tines 213 to secure the flow restrictor 200 within the vessel. The outlet flow orifice 232 is sized such that when expanded within the vessel, the orifice 232 permits only a limited flow through the vessel. As described herein, in some instances the flow restriction imposed by the flow orifice 232 is reversed to allow an increased flow. Similarly stated, in accordance with the methods described herein, the flow restrictor 200 can be manipulated to reverse the flow restriction (or otherwise increase the flow through the valve portion 230).

Figure 11:
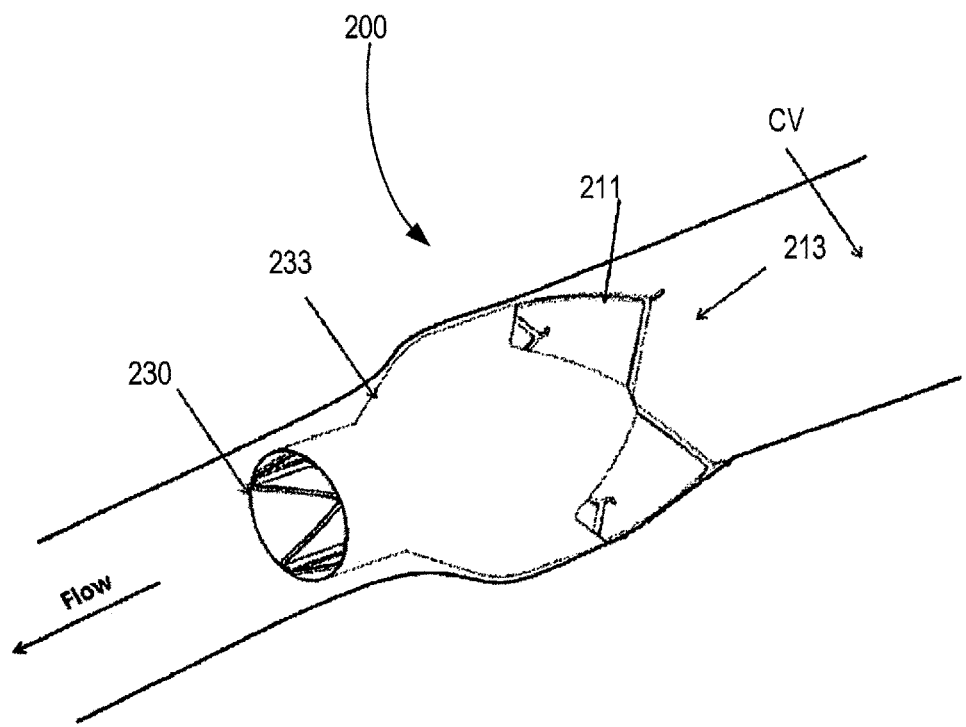
FIG. 11 is a perspective view of the reversible flow restrictor shown in FIGS. 8 and 9 deployed in a vessel in a second restriction configuration.

The outlet flow orifice 232 can be increased, as shown in FIG. 11, by any suitable method (and using any suitable mechanism) as described herein. In some embodiments, a catheter can be advanced to the flow orifice 232 and can be expanded to deform the membrane 233 and/or valve structure 231 to expand the orifice 232. For example, in some embodiments, the valve structure 231 can be initially heat-set into the low-flow (i.e., smaller orifice) configuration. Thus, the valve structure 231 can be deformed using a method such as balloon angioplasty. When the balloon is expanded, the valve structure 231 would encounter a strain rate exceeding the recoverable strain of the material, causing the structure to take permanent set in an open (or high-flow) configuration.

Figure 12:
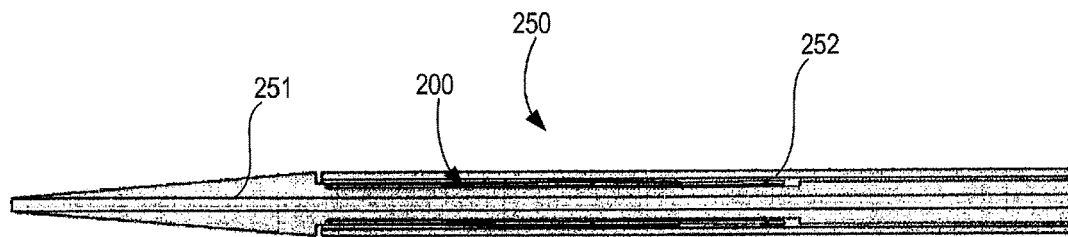
FIG. 12 is a cross-sectional side view of a delivery system according to an embodiment.

FIG. 12 shows a cross-sectional view of a catheter 250 that can be included within a kit or otherwise used to insert or manipulate any of the flow restrictors described herein. As shown the delivery catheter 250 includes a distal tip having a center lumen with a tapered dilator 251. The tapered dilator 251 is capable of tracking over the guidewire and directly into the vessel. By not using a sheath to insert the delivery catheter, the length of vessel required to deliver the device can be reduced along with the number of procedural steps. The flow restrictor 200 is constrained in a collapsed configuration with a moveable outer sheath 252. After positioned, the flow restrictor 250 is deployed by retracting the outer sheath via a mechanism on the proximal handle (not shown). After deployment the delivery catheter 250 is removed and the flow measured through the desired vessels. If needed, the diameter of the orifice can be modified as previously disclosed to achieve the desired flow rates.

Figure 13:
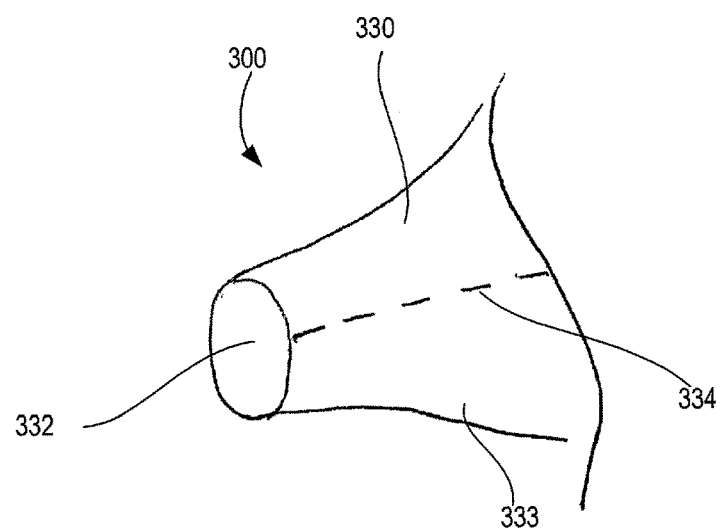
FIGS. 13 and 14 are perspective schematic illustrations of a reversible flow restrictor according to an exemplary embodiment in a first restriction configuration (FIG. 13) and in a second restriction configuration (FIG. 14).
Figure 14:
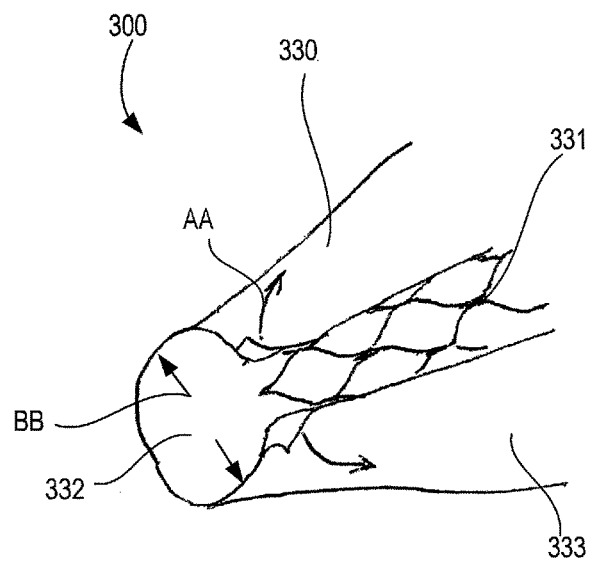

In some embodiments, a flow restrictor can include an outlet flow orifice that is defined by a shape memory allow in its high flow (or expanded) configuration. After being deployed, the size of the outlet flow orifice can be maintained in its low-flow state by the membrane (or polymer) that is disposed about the valve portion of the device. For example, FIGS. 13 and 14 are illustrations of a reversible flow restrictor 300 according to an embodiment. The reversible flow restrictor 300 is similar in many respects to the restrictor 200 described above, and is therefore not described in great detail. As shown, the reversible flow restrictor 300 includes a valve portion 330 includes an underlying structure 331 that defines an outlet flow orifice 332. The underlying structure can be any structure of the types shown and described herein, and has a default condition in a high flow (large orifice) configuration. The structure 331 is covered a membrane 333 that exerts inward forces to maintain the structure 331 in is low flow configuration, as shown in FIG. 13. The membrane 333 can be constructed from any of the materials described herein and can include a therapeutic agent.

As shown in FIG. 13, the membrane includes a perforation 334 or other suitable stress concentration riser. The perforation 334 is configured to promote deformation or tearing of the membrane in a predetermined manner when the structure 331 and/or the membrane 333 are exposed to an expansion force (e.g., via an expandable catheter or other percutaneous manipulation tool). Thus, in use, the reversible flow restrictor 300 can be manipulated while within the vessel to increase the size of the outlet flow orifice 332. For example, referring to FIG. 14, when the reversible flow restrictor 300 is manipulated, the membrane 333 will deform or tear, as shown by the arrows AA, thereby releasing the constraining force exerted on the underlying structure 331. As a result, the underlying structure 331 will move towards its default (or heat set) expanded configuration, as shown by the arrow BB.

Figure 15:
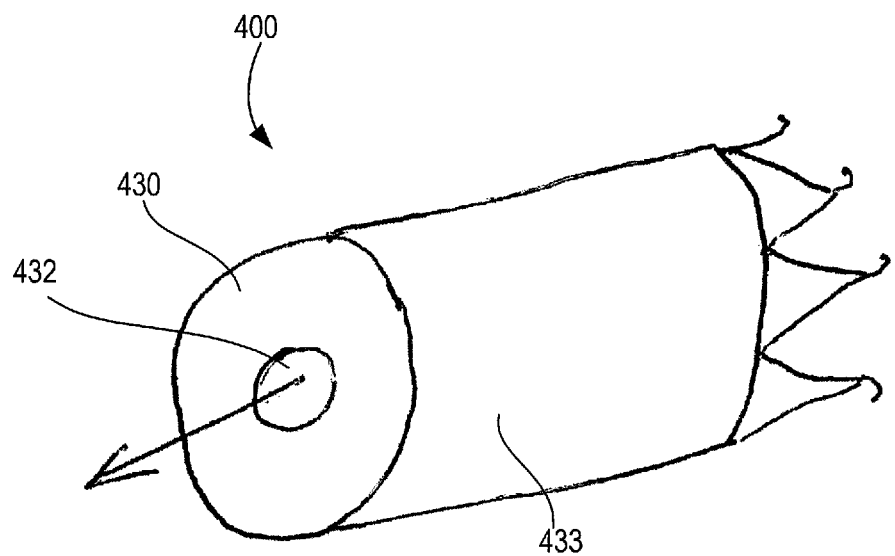
FIG. 15 is a perspective schematic illustration of a reversible flow restrictor according to an additional exemplary embodiment.
Figure 16:
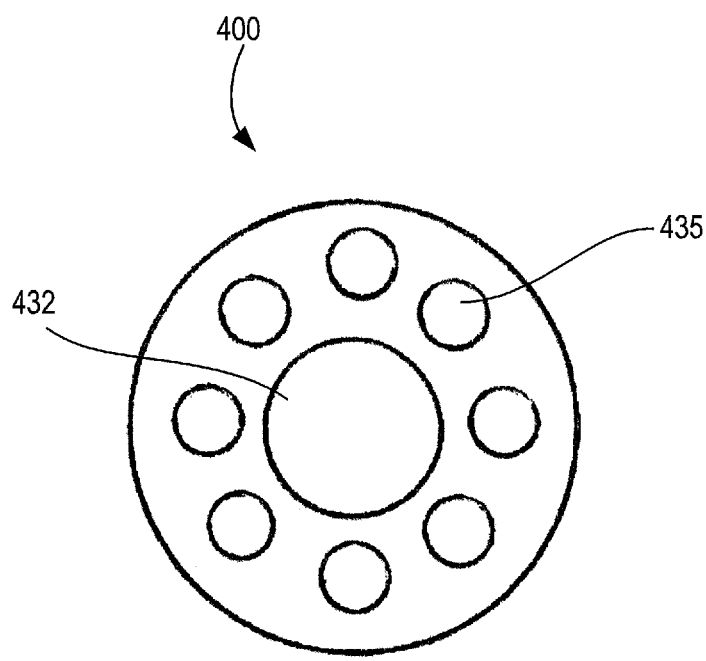
FIG. 16 is an end view of the reversible flow restrictor shown in FIG. 15.

Although the flow restrictor 200 and the flow restrictor 300 are shown as being reversible by expanding or deforming a valve structure to increase the size of the outlet orifice, in other embodiments, a flow restrictor can be reversed (i.e., the flow restriction imposed can be reversed) by any suitable mechanism. For example, in some embodiments, a flow restrictor can be reversed by selectively uncovering or exposing different flow paths, thereby allowing increased flow therethrough. For example, FIGS. 15 and 16 show a reversible flow restrictor 400 according to an embodiment. The reversible flow restrictor 400 is similar in many respects to the restrictors 200 and/or 300 described above, and is therefore not described in great detail. As shown, the reversible flow restrictor 400 includes a valve portion 430 that defines an outlet flow orifice 432, as well as a series of additional orifices 435 (see FIG. 16). The valve portion 430 is covered a membrane 433 that obstructs the additional orifices 435, as shown in FIG. 15. Note that FIG. 16 shows a side view of the restrictor 430 without the membrane 433 to clearly show the orifices 435. The membrane 433 can be constructed from any of the materials described herein and can include a therapeutic agent. In use, the reversible flow restrictor 400 can be manipulated while within the vessel to increase the flow through the valve portion 430 by uncovering or exposing one or more of the additional orifices 435. This can be done, for example, by deforming or tearing a portion of the membrane that is obstructing flow through the orifices 435.

In some embodiments, all or a portion of the membrane of any of the reversible flow restrictors can be biodegradable. In this manner, after a predetermined time period (e.g., after the primary vessel is expected to have matured), the membrane can degrade within the vessel to allow additional flow through the restricted vessel.

In some embodiments, a kit can include multiple sets of reversible flow restrictions of the types shown and described herein. For example, in some embodiments, a kit can include multiple sets of reversible flow restrictors, with each set having a different nominal "low flow rate" (i.e., the flow rate or orifice size in the collapsed configuration) and/or a different nominal "high flow rate" (i.e., the flow rate or orifice size in the expanded configuration). In some embodiments, a kit can include multiple sets of reversible flow restrictors, with each set having a different nominal time for degradation of a biodegradable portion of the restrictor. For example, some sets can be configured to maintain the flow restriction for up to 4 weeks. Other sets can be configured to maintain the flow restriction for up to 3-4 months (to allow for maturation of the primary vessel). Yet other sets can be configured to maintain the flow restriction for between about 6 months and a year.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the reversible flow restrictions are shown and described herein as being applied inside (or internal to) the collateral vessel, in other embodiments, a reversible flow restrictor can be applied outside of the collateral vessel. For example, in some embodiments, a reversible flow restrictor can be an external device that reduces the flow rate through the vessel to which it is applied without permanently rendering the vessel unusable. For example, in some embodiments, a reversible flow restrictor can include an external portion (e.g., a control portion, such as a magnetic portion) and an internal portion (e.g., a valve portion). In such embodiments, the valve portion can be inside of the collateral vessel, and the flow therethrough can be controlled and/or adjusted by the external portion.

Any of the expandable structures and/or valve structures described herein can be constructed of a shape memory allow that is configured such that its shape is self-expanding, which opposes the vessel wall to lock the flow restrictor in position and prevent migration. In some embodiments, any of the expandable structures and/or valve structures described herein can be laser cut from a single piece of tubing and heat set into shape. In other embodiments, the expandable structures and/or valve structures described herein can formed using Nitinol® wire or even laser cut Nitinol® sheet stock and heat set into a similar form.

Although the method 20 is shown and described as including placement of reversible flow restrictors 100 in the collateral vessels, in other embodiments, a method of creating an AV fistula can include placing a reversible flow restrictor in each the outlet paths, including the identified collateral vessels and the primary vessel. In this manner, the flow through all of the outlet paths is reduced. In such embodiments, the fistula can be assessed after a predetermined time period (e.g., within about 1 week, within about 2 weeks, within about 3 weeks, or within about 4 weeks) to, at that time, select the preferred primary outlet flow path. Such selection can be based on the initial performance of the vasculature. After selection, the reversible flow restrictor in the selected outlet flow path can be manipulated to allow increased blood flow therethrough. In this manner, the practitioner need not make a determination of the desired outlet flow path contemporaneously with initially forming the fistula, but rather can allow the newly-created fistula to function for a predetermined time period before determining the optimal or desired primary flow path.

Any of the flow restrictors or methods for creating or enhancing an AV fistula described herein can be employed in any suitable AV fistula site and/or can be employed with any suitable selection of vessels for the AV fistula. For example, in some embodiments, the primary blood vessel is one of a cephalic vein or a basilic vein and the secondary blood vessel is a brachial artery. The AV fistula can be a side-to-side AV fistula in an antecubital fossa region. In other embodiments, the secondary blood vessel is a radial artery and the AV fistula is a radiocephalic AV fistula.

Although the methods are described above as being beneficial to the maturation of the primary vessel, in other embodiments, the devices and methods disclosed herein can be used for other purposes associated with the creation or function of an AV fistula. For example, in some embodiments, the devices and methods disclosed herein can be used to address "Steal Syndrome." Steal Syndrome is a complication commonly associated with AV fistulas that occurs when too much flow is diverted through the anastomosis into the venous system, causing inadequate flow in the distal artery to perfuse the tissue. By placing the disclosed reversible flow restrictors in the vein (e.g., either within the collateral vessels, the primary vessels, or both), the flow in the distal artery can be increased.

In other embodiments, the devices and methods disclosed herein can be used to address excess reflux during dialysis. Reflux typically occurs in a low flow fistula where the blood being returned from the dialysis machine to the vein flows retrograde to the location of the inlet needle and re-circulates through the dialysis machine. By placing a flow restriction in the vein, between the inlet (arterial) and outlet (venous) needles, a pressure gradient is created between these locations. Since the inlet needle is located upstream (proximal) of the restriction, this will be higher pressure than the outlet needle location. This may allow the inlet and outlet needles to be placed closer together, requiring less vein length to perform dialysis In yet other embodiments, the devices and methods disclosed herein can be used to address other issues in the vasculature or any other bodily lumen. For example, in some embodiments, the devices and methods described herein can be used in connection with urological applications.

Although various embodiments have been described as having particular features and/or combinations of components, other embodiments are possible having a combination of any features and/or components from any of embodiments where appropriate. For example, any of the devices shown and described herein can include an electronic circuit system as described herein.

What is claimed is:

1. A method of enhancing an existing arteriovenous (AV) fistula, comprising:
   assessing a flow performance of a primary outflow path defined within a primary vein of the existing AV fistula between the primary vein and an artery;
   identifying a collateral vein in fluid communication with the primary vein; and
   manipulating, in response to the assessing, a reversible flow restrictor located within the collateral vein to change a blood flow rate within the primary outflow path,
   wherein the manipulating the reversible flow restrictor includes increasing a size of a flow orifice defined by a valve portion of the reversible flow restrictor to change the blood flow rate within the primary outflow path,
   wherein the reversible flow restrictor includes an expandable structure that defines the flow orifice, and a membrane about the expandable structure,
   wherein the increasing a size of a flow orifice includes
      advancing an expandable catheter assembly to the reversible flow restrictor, and
      expanding a portion of the expandable catheter assembly within the orifice to deform at least the membrane to transition the expandable structure from a first configuration to a second configuration.

2. The method of claim 1, wherein the assessing includes characterizing a maturity of the existing AV fistula by any one of determining a size of the primary vein, determining the blood flow rate within the primary outflow path, or characterizing a magnitude of a thrill produced by the existing AV fistula.

3. The method of claim 2, wherein the manipulating is performed when the maturity of the existing AV fistula is characterized as being below a target maturity level.

4. The method of claim 1, wherein the reversible flow restrictor further includes an anchor portion, the anchor portion configured to be secured within the collateral vein to maintain the reversible flow restrictor at a target location.

5. The method of claim 1, wherein the manipulating the reversible flow restrictor is performed percutaneously.

6. A method of enhancing an existing arteriovenous (AV) fistula, comprising:
assessing a flow performance of a primary outflow path defined within a primary vein of the existing AV fistula;
identifying a collateral vein in fluid communication with the primary vein; and
manipulating, in response to the assessing, a reversible flow restrictor within one of the collateral vein or the primary vein to change a blood flow rate within the primary outflow path, the reversible flow restrictor including an anchor portion and a valve portion, the anchor portion being configured to be secured within the collateral vein or the primary vein to maintain the reversible flow restrictor at a target location, the valve portion defining at least one flow orifice;
wherein manipulating the reversible flow restrictor includes increasing a size of the flow orifice to change the blood flow rate within the primary outflow path, the valve portion of the reversible flow restrictor including an expandable structure that defines the flow orifice and a membrane about the expandable structure; and
wherein increasing the size includes advancing an expandable catheter assembly to the reversible flow restrictor and expanding a portion of the expandable catheter assembly within the orifice to deform at least the membrane to transition the expandable structure from a first configuration to a second configuration.

7. The method of claim 6, wherein the assessing includes characterizing a maturity of the existing AV fistula by any one of determining a size of the primary vein, determining the blood flow rate within the primary outflow path, or characterizing a magnitude of a thrill produced by the existing AV fistula.

8. The method of claim 7, wherein the manipulating is performed when the maturity of the existing AV fistula is characterized as being below a target maturity level.

9. The method of claim 8, wherein manipulating the reversible flow restrictor is performed percutaneously.

10. The method of claim 6, wherein manipulating the reversible flow restrictor includes increasing a size of the flow orifice to change the blood flow rate within the primary outflow path.

11. A method of enhancing an existing arteriovenous (AV) fistula, comprising:
assessing a flow performance of a primary outflow path defined within a primary vein of the existing AV fistula between the primary vein and an artery;
identifying a collateral vein in fluid communication with the primary vein; and
manipulating, in response to the assessing, a reversible flow restrictor located within the collateral vein to change a blood flow rate within the primary outflow path,
wherein the manipulating the reversible flow restrictor includes increasing sizes of a plurality of flow orifices defined by a valve portion of the reversible flow restrictor to change the blood flow rate within the primary outflow path,
wherein the valve portion of the reversible flow restrictor includes a structure that defines the plurality of flow orifices, and a membrane about the structure that obstructs a portion of the plurality of flow orifices, and
wherein the increasing the size includes deforming the membrane to expose the portion of the plurality of flow orifices.

12. The method of claim 11, wherein the assessing includes characterizing a maturity of the existing AV fistula by any one of determining a size of the primary vein, determining the blood flow rate within the primary outflow path, or characterizing a magnitude of a thrill produced by the existing AV fistula.

13. The method of claim 12, wherein the manipulating is performed when the maturity of the existing AV fistula is characterized as being below a target maturity level.

14. The method of claim 11, wherein manipulating the reversible flow restrictor is performed percutaneously.

* * * * *